United States Patent
Mannheimer et al.

(10) Patent No.: US 6,553,241 B2
(45) Date of Patent: Apr. 22, 2003

(54) OXIMETER SENSOR WITH DIGITAL MEMORY ENCODING SENSOR EXPIRATION DATA

(75) Inventors: Paul D. Mannheimer, Danville, CA (US); Michael E. Fein, deceased, late of Mountain View, CA (US), by Marcia Fein, executrix; Adnan Merchant, Fremont, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 0 days.

(21) Appl. No.: 09/944,310

(22) Filed: Aug. 30, 2001

(65) Prior Publication Data

US 2002/0095078 A1 Jul. 18, 2002

Related U.S. Application Data

(60) Provisional application No. 60/229,616, filed on Aug. 31, 2000.

(51) Int. Cl.[7] .................................................. A61B 5/00
(52) U.S. Cl. ........................................ 600/323; 600/331
(58) Field of Search ............................. 600/309–310, 600/322–324, 331

(56) References Cited

U.S. PATENT DOCUMENTS

| | | |
|---|---|---|
| 3,720,199 A | 3/1973 | Rishlon et al. |
| 3,790,910 A | 2/1974 | McCormack |
| 4,303,984 A | 12/1981 | Houvig |
| 4,446,716 A | 5/1984 | Balley |
| 4,621,643 A | 11/1986 | New, Jr. et al. |
| 4,684,246 A | 8/1987 | Goldring |
| 4,700,708 A | 10/1987 | New, Jr. et al. |
| 4,734,873 A | 3/1988 | Malloy et al. |
| 4,845,649 A | 7/1989 | Eckardt et al. |
| 4,858,615 A | 8/1989 | Meinema |
| 4,862,872 A | 9/1989 | Yabe et al. |
| 4,913,150 A * | 4/1990 | Cheung et al. .............. 600/323 |
| 4,942,877 A | 7/1990 | Sakal et al. |
| 5,007,423 A * | 4/1991 | Branstetter et al. ......... 600/334 |
| 5,008,843 A | 4/1991 | Poelsler et al. |
| 5,016,198 A | 5/1991 | Schrelber |
| 5,058,588 A * | 10/1991 | Kaestle ....................... 600/323 |
| 5,070,732 A | 12/1991 | Duncan et al. |
| 5,162,725 A | 11/1992 | Hodson et al. |

(List continued on next page.)

FOREIGN PATENT DOCUMENTS

| | | |
|---|---|---|
| WO | WO93/06778 | 4/1993 |
| WO | WO97/29678 | 8/1997 |

*Primary Examiner*—Eric F. Winakur
*Assistant Examiner*—Matthew Kremer
(74) *Attorney, Agent, or Firm*—Townsend and Townsend and Crew LLP; Steven J. Cahill

(57) ABSTRACT

The present invention provides a memory chip for use in an oximeter sensor, or an associated adapter or connector circuit. The memory chip allows the storing of sensor expiration data to provide enhanced capabilities for the oximeter sensor. In addition to providing unique data to store in such a memory, the invention describes unique uses of sensor expiration data stored in such a memory.

16 Claims, 1 Drawing Sheet

U.S. PATENT DOCUMENTS

| | | |
|---|---|---|
| 5,246,003 A | 9/1993 | DeLonzor |
| 5,259,381 A | 11/1993 | Cheung et al. |
| 5,347,476 A | 9/1994 | McBean, Sr. |
| 5,365,462 A | 11/1994 | McBean, Sr. |
| 5,371,128 A | 12/1994 | Ulman et al. |
| 5,425,375 A * | 6/1995 | Chin et al. .................. 600/549 |
| 5,429,129 A | 7/1995 | Lovejoy et al. |
| 5,443,801 A | 8/1995 | Langford |
| 5,528,519 A | 6/1996 | Ohkura et al. |
| 5,645,059 A | 7/1997 | Fein et al. |
| 5,645,069 A | 7/1997 | Feln et al. |
| 5,660,163 A | 8/1997 | Schulman et al. |
| 5,720,293 A * | 2/1998 | Quinn et al. ................ 600/505 |
| 5,758,644 A * | 6/1998 | Diab et al. .................. 600/323 |
| 5,800,350 A | 9/1998 | Coppleson et al. |
| 5,830,121 A | 11/1998 | Enomoto et al. |
| 5,855,609 A * | 1/1999 | Knapp ........................ 623/914 |
| 5,987,343 A * | 11/1999 | Kinast ........................ 600/323 |
| 6,044,283 A | 3/2000 | Fein et al. |
| 6,104,938 A * | 8/2000 | Huiku et al. ................ 600/322 |
| 6,241,679 B1 * | 6/2001 | Curran ........................ 600/485 |
| 6,298,255 B1 * | 10/2001 | Cordero et al. ............. 600/372 |
| 6,308,089 B1 * | 10/2001 | von der Ruhr et al. ..... 600/338 |
| 6,356,774 B1 * | 3/2002 | Bernstein et al. ............ 600/323 |
| 6,360,114 B1 * | 3/2002 | Diab et al. .................. 600/336 |
| 6,377,829 B1 * | 4/2002 | Al-Ali ........................ 600/323 |
| 6,463,310 B1 * | 10/2002 | Swedlow et al. ........... 600/323 |
| 6,466,808 B1 * | 10/2002 | Chin et al. .................. 600/323 |

* cited by examiner

OXIMETER SENSOR WITH DIGITAL MEMORY ENCODING SENSOR EXPIRATION DATA

CROSS-REFERENCES TO RELATED APPLICATIONS

This application claims priority to U.S. Provisional Patent Application No. 60/229,616, filed Aug. 31, 2000, which is hereby incorporated by reference herein.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

An encoding mechanism is shown in U.S. Pat. No. 4,700,708, the disclosure of which is incorporated herein by reference. This mechanism relates to an optical oximeter probe which uses a pair of light emitting diodes (LEDs) to direct light through blood-perfused tissue, with a detector picking up light which has not been absorbed by the tissue. The operation depends upon knowing the wavelength of the LEDs. Since the wavelength of LEDs can vary, a coding resistor is placed in the probe with the value of the resistor corresponding to the actual wavelength of at least one of the LEDs. When the oximeter instrument is turned on, it first applies a current to the coding resistor and measures the voltage to determine the value of the resistor and thus the value of the wavelength of the LED in the probe.

U.S. Pat. No. 5,259,381 recognizes that the coded value of the wavelength of the red LED provided by a coding resistor may be inaccurate, since the actual wavelength can vary with temperature. Accordingly, this patent teaches including a temperature sensor in the oximeter probe to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877 assigned to Minolta. This patent discloses using an EPROM memory to store digital information, which can be provided in parallel or serially from the sensor probe to the remote oximeter. The memory is described as storing coefficients for the saturation equation, wavelength, sub-wavelength (where 2 peaks for LED), half-width of wavelength spectrum emitted by LED, intensity of LEDS or ratio, and on time of LEDS (written by the processor).

Other examples of coding probe characteristics exist in other areas. Multiple calibration values are sometimes required, with this making the circuitry more complex or requiring many leads. In U.S. Pat. No. 4,446,715, assigned to Camino Laboratories, Inc., a number of resistors are used to provide coded information regarding the characteristics of a pressure transducer. U.S. Pat. No. 3,790,910 discloses another pressure transducer with a ROM storing characteristics of the individual transducer. U.S. Pat. No. 4,303,984 shows another probe with digital characterization information stored in a PROM, which is read serially using a shift register.

Typically, the coding element is mounted in the probe itself. For instance, U.S. Pat. No. 4,621,643 shows the coding resistor mounted in the probe element itself In addition, U.S. Pat. No. 5,246,003 shows the coding resistor being formed with a printed conductive material on the probe itself.

In some devices, an electrical connector coupled by a cable to a device attached to a patient may include a coding element. For example, U.S. Pat. No. 3,720,199 shows an intra-aortic balloon catheter with a connector between the catheter and a console. The connector includes a resistor with a value chosen to reflect the volumetric displacement of the particular balloon. U.S. Pat. No. 4,684,245 discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

U.S. Pat. No. 5,645,059 teaches using a modulated signal to provide the coded data to a remote analyzer. U.S. Pat. No. 5,429,129 shows using a voltage regulator to produce a specific voltage value in response to an attempt to read by the analyzer.

Hewlett-Packard Company U.S. Pat. No. 5,058,588 teaches an oximeter sensor with an encoding element that could be resistor, ROM, or customized integrated circuit. The encoding element encodes the type of sensor (in particular, type indicating area of placement on body—finger, ear, foot, arm; also, the type of sensor can indicate transmission/reflection type, or adult/neonate {indicating correction to be performed on theoretical oxygen saturation, allow switching between physiological limits such as minimum/maximum pulse rates for adults/neonates}; the maximum driving current may be adapted according to type of sensor, and contact of sensor with tissue can be tested by means of an attenuation measurement if sensor type is known).

Nellcor U.S. Pat. No. 5,645,059, the disclosure of which is hereby incorporated herein by reference, teaches coding information in sensor memory used to provide pulse modulated signal, to indicate the type of sensor (finger, nose), the wavelength of a second LED, the number of LEDs, the numerical correction terms to the standard curves, and an identifier of the manufacturer.

A number of catheter patents also discuss encoding information in the catheter. Sentron U.S. Pat. No. 4,858,615 teaches encoding the type of sensor, type number, serial number, date of production, safe use life of the sensor, correction data for non-linearity, pressure sensitivity, offset, and temperature sensitivity.

Interflo Medical Published PCT Application No. PCT/US92/08263, Publication No. WO 93/06776 teaches encoding patient specific data, size, manufacture date, batch number, sterilization date, expiration date, transducer number and type, manufacturer's name and address, thermistor heating element resistance, filament efficiency, program segments or patient historical data, format version for the calibration data, trademark information, catheter unique serial number, ship date, other date and time information, security code to identify manufacturer, thermal mass, filament composition, coefficient of resistance, layout byte, checksum, copyright, number of seconds since a certain date, patient weight, patient height, timestamp of 1st CO data point, and a count of all CO data points in EEPROM.

Dulex-Ohmeda of Boulder, Colo. markets an oximeter sensor product that encodes data into resistor values representing pointers to a lookup table containing coefficients (as in U.S. Pat. No. 4,700,708) as well as indicating a range of LED drive current to use with the sensor. The LEDs are driven with a higher or lower drive currents depending upon the value of the resistor in a particular sensor.

Honeywell U.S. Pat. No. 4,303,984 (expires Dec. 14, 1999) describes a memory which stores characterization information, such as linearization information for a pressure sensor. Alnor Instrument U.S. Pat. No. 5,162,725 describes storing both calibration and ID information in a sensor memory. Seimans U.S. Pat. No. 5,016,198 describes a coding memory in a sensor with data for defining sensor's characteristic curve. McBean U.S. Pat. No. 5,365,462 describes a date code in a sensor memory. Honeywell U.S. Pat. No. 4,734,873 describes a pressure sensor with a PROM storing coefficients for a polynomial. Robert Bosch U.S. Pat. No. 4,845,649 describes a PROM in a sensor storing correcting data.

McBean U.S. Pat. No. 5,371,128 relates to EEPROM in sensor with sensor type code and calibration data. McBean U.S. Pat. No. 5,347,476 describes an accuracy code. Otax U.S. Pat. No. 5,528,519 shows a PROM in a connector for oximeter.

Square D Company U.S. Pat. No. 5,070,732 shows calibration data in a sensor memory. Baxter U.S. Pat. No. 5,720,293 talks about different calibration information for a catheter, including a security code (encryption is discussed), serial number, model number, ID data such as calibration, manufacture, sterilization and ship date or other date and time information, a software program segment, security code for identifying whether sensor made by same manufacturer as monitor manufacturer, filament or transducer resistance, heat transfer coefficient, thermal mass, filament composition and coefficient of resistance, layout byte, copyright notice, checksum, random data bytes. Porsche U.S. Pat. No. 5,008,843 describes a sensor with EEPROM ID and characteristics data.

BRIEF SUMMARY OF THE INVENTION

The present invention provides a memory chip for use in an oximeter sensor, or an associated adapter or connector circuit. The memory chip allows the storing of sensor expiration data to provide enhanced capabilities for the oximeter sensor. In addition to providing unique data to store in such a memory, the invention describes unique uses of sensor expiration data stored in such a memory.

DETAILED DESCRIPTION OF THE INVENTION

Figure 1:
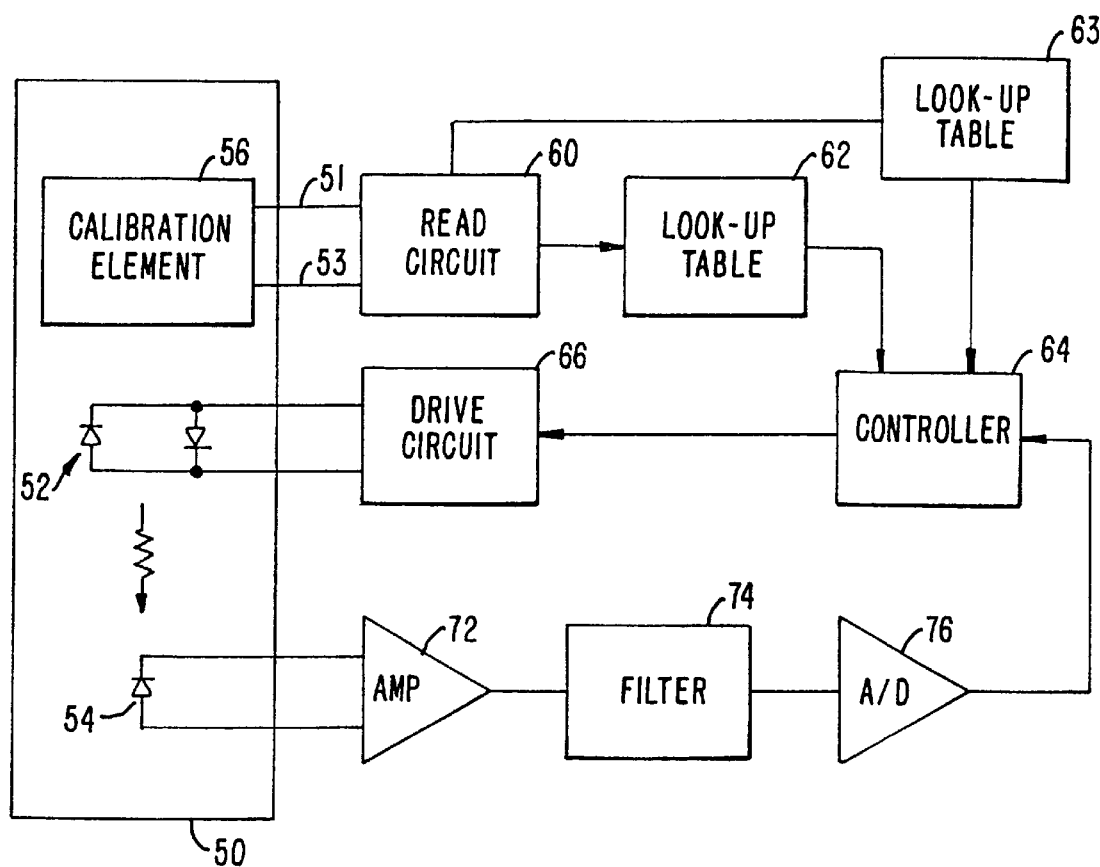
FIG. 1 is a block diegram of a pulse oximeter system in accordance with the present invention.

FIG. 1 is a block diagram of a pulse oximeter system incorporating a calibration memory element 56 according to the invention. In one embodiment, memory element 56 is a two-lead semiconductor digital memory chip. The calibration element is part of the sensor 50 which also includes red and infrared LEDs 52 as in the prior art, along with a detector 54. If desired, LEDs 52 may be replaced with other light emitting elements such as lasers.

The oximeter includes read circuit 60, drive circuit 66, look-up tables 62 and 63, controller 64, amplifier 72, filter 74, and analog-to-digital converter 76. Read circuit 60 is provided for reading multiple coded values across the two leads 51, 53 connected to calibration element 56. One value is provided to a look-up table 62 to determine appropriate wavelength dependent coefficients for the oxygen saturation calculation, as in the prior art. The other value(s) are then provided to another look up table(s) 63 which provides input (e.g., coefficients) to other calculations performed by controller 64. These additional calculations may enhance the performance and/or safety of the system. Controller 64 provides signals to a drive circuit 66, to control the amount of drive current provided to LEDs 52. Memory 56 may, for example, be implemented as a random access memory (RAM), a FLASH memory, a programmable read only memory (PROM), an electrically erasable PROM, a similar programmable and/or erasable memory, any kind of erasable memory, a write once memory, or other memory technologies capable of write operations.

As in the prior art, detector 54 is connected through an amplifier 72 and a filter 74 to an AID converter 76. This forms a feedback path used by controller 64 to adjust the drive current to optimize the intensity range of the signal received. For proper operation the signal must be within the analog range of the circuits employed. The signal should also be well within the range of A/D converter 76 (e.g., one rule that may be applied is to adjust LED drives and amplifier gains so that both red and IR signals fall between 40% and 80% of full scale reading of converter 76). This requires correct and independent settings for both the red and infrared LEDs.

Embodiments of the present invention include several uses of memory 56. In a first embodiment of the present invention, sensor expiration data is digitally encoded into memory 56 at the time of its manufacture. Memory 56 could encode an expiration date after which time the sensor can no longer be certified as being effective. The oximeter monitor includes a timer that keeps track of the present date and year. Controller 64 is preprogrammed to check the date recorded in memory 56 each time the sensor is used. If controller 64 determines that the expiration date encoded in memory 56 is earlier or the same as the present date, the oximeter monitor displays an error message on a display screen indicating that the sensor has expired. If desired, the oximeter monitor may shut off the circuitry (such as drive circuit 66) that operates the sensor or briefly run a high current through LEDs 52 to disable them until the monitor determines that the sensor has been replaced.

Another embodiment of the present invention relates to product sterilization cycles. Sterilization (e.g., using ethylene trioxide) may be performed on a medical oximeter sensor during manufacture to sterilize the sensor using techniques that are well-known to those of skill in the art. Typically, the effectiveness of the sterilization can be guaranteed for a finite amount of time, commonly, one or two years.

The date of the sterilization can be digitally encoded into memory 56. The oximeter monitor can read the date that sterilization was performed from memory 56 and compare the date to an expiration date (also encoded into memory 56). If the current date is beyond the expiration date, the oximeter monitor can display an error message or refuse to function until the sensor is replaced.

In another embodiment of the present invention, a sensor usage time limit is preprogrammed into memory 56 at the time that sensor 50 is manufactured which indicates the maximum amount of time that the sensor can be used for monitoring blood oxygen saturation and other patient parameters before parts of the sensor typically become degraded. The elapsed time of sensor usage is monitored by the controller 64 or other circuitry in the oximeter monitor and digitally written into memory chip 56. The monitored sensor usage time may, for example, correspond to the total amount of time current is driven through the LEDs or the total amount of time signals are received from the photodetector for a particular sensor.

As the sensor is used for pulse oximetry, usage time is monitored for each use and recorded into memory 56. The sensor usage time for each use can be periodically added to the usage time from prior uses, and the total usage time can be determined and recorded in memory 56. The oximeter monitor reads the maximum time limit from memory 56 and compares it to the total time usage for the sensor to determine if the sensor has expired. The maximum time limit is typically greater for reusable sensors than for single-use sensors.

After the memory-programmed maximum time limit has been reached or exceeded, the sensor "expires." When the sensor expires, for example, the oximeter monitor may refuse to function with the expired sensor and would indicate that a fresh sensor is needed. As another example, the oximeter monitor displays a sensor expired message when the sensor expires. Furthermore, the sensor could be disabled by briefly running a high current through the LEDs, or by other means, to prevent further use of the sensor.

In another embodiment of the present invention, the date of expiration of the sensor warranty could be written into memory chip 56 (similar to the expiration date). The warranty expiration date may be a specific date or a warranty time period. For example, the warranty expiration date may be 2, or 6, or 12, etc. months from the date of manufacture or the date of first use of the sensor. The warranty time period and the date of manufacture (or a specific warranty expiration date) may be encoded into memory 56 of each sensor unit during the manufacturing process. The date of first use may be encoded into memory 56 of a sensor unit by controller 64 when the sensor unit is first connected to an oximeter monitor.

Controller 64 reads memory 56 to determine if an initial use date has been recorded. If no date has been recorded, controller 64 obtains the current date from a timer and records that date into memory 56. If an initial use date or manufacture date has been encoded into memory 56, controller 64 can calculate the warranty expiration date from memory 56 (by adding the initial use or manufacture date to the warranty time period) when the sensor is connected to the oximeter.

The oximeter monitor instrument gives some indication of the sensor warranty expiration date as appropriate by reading the warranty expiration date data in memory 56. For example, the oximeter monitor may display the warranty expiration date for a sensor on a display screen each time the sensor is connected to the oximeter or when prompted by the user. The oximeter monitor can compare the warranty expiration date with the current date to determine if the warranty has expired and display a warranty expiration message.

Disposable oximeter sensors can be sterilized and reconstructed at the factory so that they can be used with a different patient. Each time a sensor is recycled at the factory, a counter number stored in sensor memory 56 can be incremented. The counter number can be used to prevent operation of the sensor if it has been recycled more than the allowed number of times (e.g., 3 times). The maximum number of allowed recycles can also be encoded into memory 56. A digital memory reading device can read the number of times that the sensor has been recycled from memory 56. If the sensor has been recycled the allowed number of times, then the sensor is discarded. If the sensor has been recycled less than the allowed number of times, the counter number in memory 56 is incremented and the sensor is sterilized and reused.

If desired, controller 64 may also read the counter number and the maximum recycle number from memory 56 each time the sensor is used to determine if the counter exceeds a maximum number of recycles. If the counter exceeds the maximum, the oximeter monitor may refuse to operate until the sensor is replaced, or disable the sensor by briefly running a high current through the LEDs.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiments disclosed, but that the invention will include all embodiments and equivalents falling within the scope of the claims.

What is claimed is:

1. An oximeter sensor comprising:
   a light emitting element;
   a light detecting element; and
   a memory device for storing digital data comprising expiration data relating to the oximeter sensor,
   wherein an oximeter monitor coupled to said oximeter sensor briefly drives a high current through said light emitting element to disable said light emitting element after an expiration date stored in the memory device.

2. The oximeter sensor of claim 1 wherein said expiration data comprises a sensor warranty expiration date.

3. The oximeter sensor of claim 1 wherein said expiration data is an expiration date after which time said sensor can no longer be certified as being effective.

4. The oximeter sensor of claim 1 wherein said expiration data is a date after which time sterilization should not be performed on said sensor.

5. The oximeter sensor of claim 1 wherein said expiration data comprises:
   a counter that encodes the number of sterilization cycles that have been performed on said sensor; and
   a maximum number of sterilization cycles allowed for said sensor.

6. The oximeter sensor of claim 1 wherein said expiration data comprises a maximum usage time for the use of said oximeter sensor.

7. The oximeter sensor of claim 6 wherein said expiration data further comprises a total usage time to date for said oximeter sensor.

8. The oximeter sensor of claim 7 wherein an oximeter monitor coupled to said oximeter sensor encodes the total usage time for said sensor in said memory device and compares the total usage time to said maximum usage time to determine when said sensor has expired.

9. A method for storing data in an oximeter sensor, the method comprising
   emitting light from a light emitting element;
   detecting light from the light emitting element using a photodetector;
   storing digitally encoded data in a memory in the sensor, the digitally encoded data comprising expiration data relating to the oximeter sensor; and
   driving a high current through said light emitting element to disable said light emitting element after an expiration date stored in the memory.

10. The method of claim 9 wherein storing said digitally encoded data further comprises storing a sensor warranty expiration date in said memory.

11. The method of claim 9 wherein storing said digitally encoded data further comprises storing an expiration date in said memory after which time said sensor cannot be certified as being effective.

12. The method of claim 9 wherein storing said digitally encoded data further comprises storing an expiration date after which time sterilization cycles should not be performed on said sensor.

13. The method of claim 9 wherein storing said digitally encoded data further comprises storing a counter that encodes the number of sterilization cycles that have been performed on said sensor and a maximum number of sterilization cycles allowed for said sensor in said memory.

14. The method of claim 9 wherein storing said digitally encoded data further comprises storing a maximum usage time for the use of said oximeter sensor.

15. The method of claim 14 wherein storing said digitally encoded data further comprises storing a total usage time to date for said oximeter sensor.

16. The method of claim 15 further comprising:
   displaying a sensor expiration message on a display screen when the total usage time for said sensor reaches the maximum usage time.

* * * * *